US007769138B2

(12) United States Patent
Dafni

(10) Patent No.: US 7,769,138 B2
(45) Date of Patent: Aug. 3, 2010

(54) APPARATUS AND METHOD OF IMPROVED ANGIOGRAPHIC IMAGING

(75) Inventor: Ehud Dafni, Caesarea (IL)

(73) Assignee: CMT Medical Technologies Ltd., Yokneam Ilit (IL)

(*) Notice: Subject to any disclaimer, the term of this patent is extended or adjusted under 35 U.S.C. 154(b) by 480 days.

(21) Appl. No.: 10/599,279

(22) PCT Filed: Mar. 29, 2004

(86) PCT No.: PCT/IL2004/000282

§ 371 (c)(1),
(2), (4) Date: Sep. 25, 2006

(87) PCT Pub. No.: WO2005/092187

PCT Pub. Date: Oct. 6, 2005

(65) Prior Publication Data

US 2007/0242802 A1 Oct. 18, 2007

(51) Int. Cl.
*H05G 1/64* (2006.01)
(52) U.S. Cl. .................. 378/98.11; 378/98.12
(58) Field of Classification Search .......... 378/98.8, 378/98.9, 98.11, 98.12, 62
See application file for complete search history.

(56) References Cited

U.S. PATENT DOCUMENTS 4,393,402 A * 7/1983 Keyes et al. .......... 378/98.11

| 4,662,379 | A | 5/1987 | Macovski |
| 6,356,617 | B1 | 3/2002 | Besch et al. |
| 6,408,050 | B1 * | 6/2002 | Han et al. .......... 378/98.9 |
| 2005/0017189 | A1 * | 1/2005 | Homma et al. .......... 250/370.11 |

OTHER PUBLICATIONS

Mikulec. "Development of Segmented Semiconductor Arrays for Quantum Imaging". Nuclear Instruments & Methods in Phys. Research A 510 (2003) 1-23.
El-Hanany et al. "CZT Pixel-Detectors Equipped with Effective Ohmic . . .". Hard X-Ray, Gamma-Ray, and Neutron Physics. Proceedings of SPIE, Denver, Colorado, Jul. 19-23, 1999.
El-Hanany et al. "CZT Pixel-Detector Modules . . .". Presented at the 11th International Workshop on Room Temperature Semiconductor X and Gamma Detectors; Vienna Oct. 11-15, 1999.
Narita et al. "Development of IMARAD CZT Detectors with PIN Contacts". 1999, Proc SPIE 3768.
Narita et al. "Design and Preliminary Tests of a Prototype CZT Imaging Array". 2002, Proc SPIE, 4497, 79, brought herein as references.
Fanti et al. "Medipix Parallel Readout . . .". Proc. of the IEEE Nuclear Science Symposium and Medical Imaging Conference, San Diego, California, Nov. 4-10, 2001, M7-4.

* cited by examiner

*Primary Examiner*—Jurie Yun
(74) *Attorney, Agent, or Firm*—William H. Dippert; Eckert Seamans Cherin & Mellott, LLC

(57) ABSTRACT

The x-ray tube is energized (12) and the myocardium is imaged (16) while contrast agent is infused to the coronary arteries of the subject (14). Single photon counting data acquired with the detector while two thresholds are set to form simultaneously low energy images and high energy images (16). The images are processed (18) and displayed (20).

28 Claims, 5 Drawing Sheets

APPARATUS AND METHOD OF IMPROVED ANGIOGRAPHIC IMAGING

FIELD OF THE INVENTION

The present invention relates to digital x-ray imaging. More particularly, the present invention relates to an apparatus for coronary and general angiography and a method of increasing image contrast and reducing image artifacts.

BACKGROUND OF THE INVENTION

X ray imaging is a common tool used in cardiovascular angiography. Blood vessels are imaged, usually in fluoroscopic mode up to 30 frames per second, while being infused with Iodine based contrast agent. It is a highly desired purpose to increase the image contrast of the blood vessels relative to the surrounding tissues so as to facilitate the interpretation of the results. In the same time, it is highly necessary to reduce radiation dose to which the examined subject as well as personnel are exposed.

One common technique to improve visual contrast is digital subtraction angiography (DSA). In DSA, a "mask" image is acquired before infusion of Iodine contrast agent and subsequently subtracted from images with Iodine contrast. In this way, the appearance of blood vessels is amplifying. However, DSA is artifacts prone due to motion of the patient between the time the mask is acquired and the time the contrast images are acquired. Therefore, DSA is not usually used in coronary angiography as the coronary arteries are at a constant motion due to the heart activity.

Another common technique to improve image contrast and differentiate better between absorbing element composition is dual energy subtraction. According to this technique, the subject is imaged twice with two different energy spectra of the X ray source. Different energy spectra may be obtained by applying different X ray tube voltage, different tube anode material, different beam filtering or a combination of the above. A category within this technology is K edge subtraction imaging where the two energy spectra are chosen so one spectrum peaks below the K edge of a material of interest, say Iodine, and the other peaks just above the K edge. However, this technique is not applicable to cardiac angiography with conventional X ray sources as the time to alternate between two energies is relatively long and does not allow for motion artifact free image subtraction.

U.S. Pat. No. 6,356,617 discloses a device for energy subtraction cardiac angiography based on irradiating the patient with monochromatic X ray beam from synchrotron radiation at two alternating energies. However, monochromatic X ray beams with sufficient intensity are available in just a few synchrotron radiation accelerator laboratories worldwide, so this solution is not practical for routine applications.

Practically, all X ray detectors currently in use in medical imaging are based on the principle of charge integration. Detector elements convert incoming X rays to electric charge, charge from many X rays is integrated for a certain time window and the signal is digitized to provide the output signal for the detector element. This description applies to various detectors in use in medical X ray imaging systems, regardless of the technology of the detector.

Because the radiation from X ray tubes come at a wide spectrum of energies and the charge generated by each X ray is proportional to the energy transferred from the X ray to the detector, the signal in conventional detectors is proportional to the sum of the X rays times their energy rather than simply to the number of X rays. Therefore, the output signal is biased to higher energy photons. Higher energy photons carry less diagnostic information than lower energy photons, as they are less sensitive to differences between tissues in the body, so the image contrast is reduced as compared to a theoretical system that does not bias the output to higher energy photons. On the other hand, gamma cameras and PET scanners are based on single photon counting. In these devices, each photon is counted separately and the output signal is purely the number of photons detected in a detector element.

The advantage of single photon counting for X ray imaging is recognized and a number of devices have been developed and tested. The following extensive review is brought herein as reference: B. Mikulec "Development of segmented semiconductor arrays for quantum imaging" Nuclear Instruments & Methods in Phys. Research A 510 (2003) 1-23.

The devices under discussion are built of a matrix of X ray detection elements, each element connected to a separate signal processing circuitry. The electronics provides a digital count of the number of photons detected by each element in a given time frame.

It was also realized (same reference) that by segmenting the imaging data according to X ray photon energy, images of higher image contrast might be achieved. This can be achieved e.g. by setting thresholds on each photon signal level and counting separately photons at two or more energy bins.

Incorporating detection devices enabling single photon counting in an apparatus for angiographic X ray imaging, especially for coronary angiography, provides a new and improved apparatus by which motion artifacts generated from heart beats and breathing movements are substantially eliminated.

SUMMARY OF THE INVENTION

It is an object of the present invention to provide a method and apparatus for improved X ray imaging of coronary angiography so as to eliminate heart motion artifacts and breathing artifacts.

It is another object of the present invention to provide a method and apparatus for improved X ray imaging of peripheral angiography so as to eliminate any motion artifacts.

It is yet another object of the present invention to provide a method and apparatus for improved X ray imaging in non-cardiovascular applications, for example: dynamic orthopedic imaging of bones or joint during motion, amplification of micro-calcifications in Mammography, etc.

It is thus provided in accordance with one aspect of the present invention an apparatus for improved angiographic X ray imaging of a subject's body infused with contrast agent, said apparatus comprising:

an x ray source adapted to emit X rays directed to pass through the subject's body wherein said X ray beam is polychromatic;

a sensor system adapted to receive attenuated X rays that passed through the subject's body, wherein said sensor comprises detection means divided into a plurality of detector elements, wherein each one of said plurality of detection elements is adapted to convert photon energy of a portion of said attenuated X rays into electric charges;

at least one readout chip divided into a plurality of channels wherein each one of said plurality of channels is electronically connected to one of said plurality of detection elements and wherein each one of said plurality of channels is adapted to convert said electric charges into digital data;

acquisition system adapted to receive said digital data from said sensor and generate at least two electronic representations wherein one of said at least two electronic representations is attained from low energy photons and another one of said at least two electronic representations is attained from high energy photons wherein said at least two electronic representations are measured simultaneously at the subject and at a certain position of said X ray source;

processing means adapted to manipulate said at least two electronic representations into at least one image;

displaying means adapted to display said at least one image; whereby said at least one image attained from at least two energy bins amplify the appearance of the contrast agent in the blood vessels in respect with the surrounding tissues of the subject's body.

Furthermore, in accordance with another preferred embodiment of the present invention, said detection means is a pixel detector chip made of a semiconductor material.

Furthermore, in accordance with another preferred embodiment of the present invention, said semiconductor material is selected from a group of semiconductor materials such as Cadmium Zinc Telluride (CZT).

Furthermore, in accordance with another preferred embodiment of the present invention, said detection means is a detector chip made of a scintillator material coupled to light to charge conversion elements.

Furthermore, in accordance with another preferred embodiment of the present invention, said scintillator material is selected from a group of materials such as CsI or CsI(Tl).

Furthermore, in accordance with another preferred embodiment of the present invention, said light to charge conversion elements comprise an array of Si photodiodes.

Furthermore, in accordance with another preferred embodiment of the present invention, said at least one readout chip is provided with at least two programmable threshold discriminators so as to allow each one of said plurality of channels to output a representation of a number of photons carrying energy below a predetermined threshold, between said predetermined threshold and a higher predetermined threshold, and above said higher predetermined threshold.

Furthermore, in accordance with another preferred embodiment of the present invention, said at least one readout chip is provided with a preamplifier and a pulse shaper.

Furthermore, in accordance with another preferred embodiment of the present invention, further comprising at least two counters adapted to count events detected in at least two programmable threshold discriminators.

Furthermore, in accordance with another preferred embodiment of the present invention, the infused contrast agent is Iodine solution.

Furthermore, in accordance with another preferred embodiment of the present invention, said low energy photons are set below the K edge of the contrast agent and said high energy photons are set above the K edge of the contrast agent.

Furthermore, in accordance with another preferred embodiment of the present invention, said low energy photons are set just above the K edge of the contrast agent and said high energy photons are set further above the K edge of the contrast agent.

Furthermore, in accordance with another preferred embodiment of the present invention, a portion of the subject's body is the chest and wherein coronary blood vessels are imaged.

Furthermore, in accordance with another preferred embodiment of the present invention, a difference image of said low energy photons presentation and said high energy photons presentation is generated and displayed so as to amplify the appearance of the contrast agent, wherein said difference image is motion artifacts prone.

Furthermore, in accordance with another preferred embodiment of the present invention, a portion of the subject's body is the head and neck and wherein cranial or cranial supply blood vessels are imaged.

Furthermore, in accordance with another preferred embodiment of the present invention, peripheral blood vessels are imaged.

Furthermore, in accordance with another preferred embodiment of the present invention, images are acquired, processed and displayed multiple times every second at a short time lag from acquisition so as to generate real time imaging of the subject's body.

Furthermore, in accordance with another preferred embodiment of the present invention, said processing means is adapted to process said at least two electronic representations by producing a normalized high energy image of one of the electronic representation attained from high energy photons to another electronic representation attained from low energy photons and subtraction of said normalized high energy image from said another electronic representation.

Furthermore, in accordance with another preferred embodiment of the present invention, said processing means is adapted to process said at least two electronic representations by producing a normalized high energy image of one of the electronic representation attained from high energy photons to another electronic representation attained from low energy photons and subtraction of a pre-determined fraction of the normalized high energy image from said another electronic representation.

In accordance with another aspect of the present invention, it is provided a method for producing images of improved X ray angiography of a subject's body, said method comprising:

directing polychromatic X ray beam to pass through the subject's body;

positioning a sensor system adapted to receive attenuated X rays that passed through said subject's body, said sensor system comprising detection means divided into a plurality of detector elements, wherein each one of said plurality of detection elements is adapted to convert photon energy of a portion of said attenuated X rays into electric charges, and at least one readout chip provided with at least two discriminators, said at least one readout chip divided into a plurality of channels wherein each one of said plurality of channels is electronically connected to one of said plurality of detection elements and wherein each one of said plurality of channels is adapted to convert said electric charges into digital data;

setting threshold levels for said at least two discriminators for each one of said plurality of channels;

injecting a contrast agent into blood vessels of the subject's body;

positioning said subject so that X ray beam passes through the body of the subject and attenuated X rays that passed through the subject's body are received by said sensor system;

acquiring single photon counting data so as to simultaneously establish at least two images from at least one of low photon energy window and at least one of high energy window;

Processing said at least two images so as to provide high contrast and motion artifact free image of the subject's blood vessels.

Furthermore, in accordance with another preferred embodiment of the present invention, said low energy window is set below the K edge of said contrast agent and said high energy window is set above the K edge of said contrast agent.

Furthermore, in accordance with another preferred embodiment of the present invention, said low energy window is set just above the K edge of said contrast agent and said high energy window is set further above the K edge of said contrast agent.

Furthermore, in accordance with another preferred embodiment of the present invention, setting threshold levels comprises irradiating said detecting means with radiation of at least two predetermined energy levels while monitoring output counting rate so as to set the threshold level slightly below the level in which the count rate drops.

Furthermore, in accordance with another preferred embodiment of the present invention, said detecting means is irradiated with X ray photons at 32 keV for setting one threshold level and with gamma rays of 59.5 keV for setting a second threshold level.

Furthermore, in accordance with another preferred embodiment of the present invention, said processing said at least two images comprises
   normalizing one of said at least two images attained from said high energy window to another image attained from said low energy window so as to acquire normalized high energy image;
   subtracting said normalized high energy image from said another image attained from said low energy image.

Furthermore, in accordance with another preferred embodiment of the present invention, said processing said at least two images comprises
   normalizing one of said at least two images attained from said high energy window to another image attained from said low energy window so as to acquire normalized high energy image;
   subtracting a pre-determined fraction of the normalized high energy image from said low energy image.

Furthermore, in accordance with another preferred embodiment of the present invention, the method is used to image the subject's coronary blood vessels.

Furthermore, in accordance with another preferred embodiment of the present invention, the subject's body is the head and neck and wherein cranial or cranial supply blood vessels are imaged.

Furthermore, in accordance with another preferred embodiment of the present invention, peripheral blood vessels are imaged.

BRIEF DESCRIPTION OF THE FIGURES

In order to better understand the present invention and appreciate its practical applications, the following Figures are attached and references herein. Like components are denoted by like reference numerals.

It should be noted that the figures are given as examples and preferred embodiments only and in no way limit the scope of the present invention as defined in the appending Description and Claims.

DETAILED DESCRIPTION OF THE INVENTION AND THE FIGURES

Figure 1:
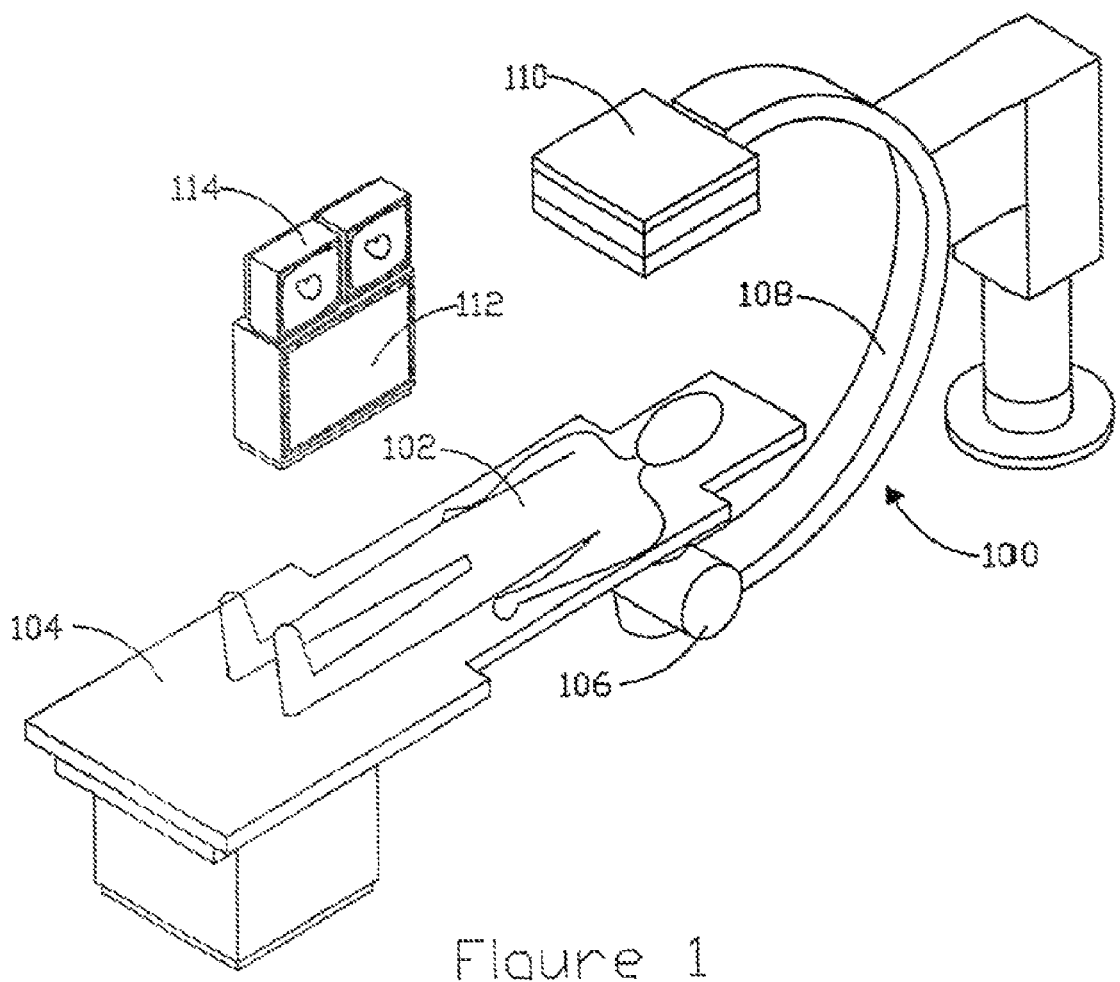
FIG. 1 illustrates a subject examined in an apparatus for improved imaging in accordance with a preferred embodiment of the present invention.

The present invention provides a new and unique method and apparatus for improved X ray imaging to be used especially in cardiovascular angiography that allows a reduced radiation dosage to be applied onto the examined subject while attaining better results of the examined blood vessels in respect with contrast. Another advantage of the method of the present invention is that reference images are unnecessary for background subtraction so that motion-prone artifacts generated from heart beats or breathing motions are substantially eliminated.

It is well known to experts in the art that X ray photons with energies just above the k edge of Iodine (33.2 keV) provide higher image contrast of Iodine infused arteries than X ray photons with energies below the k edge energy or with significantly higher energies. Embodiments described herein after refer to typical X ray system for chest imaging with generator voltage of typically 100-120 kVp and filtering of X ray photons at energies typically below 20 keV; hence, the energy spectrum typically spreads between 20 keV and 120 keV. Using such a spectrum for imaging contrast enhanced arteries, the image of the low energy photons minus the image of the high energy photons has an enhanced display of the arteries while suppressing the soft tissue. Generally and in accordance with a preferred embodiment of the present invention, a patient is imaged in a coronary or general angiography setting where imaged arteries are infused with contrast agent. No contrast-less mask needs to be taken ahead of contrast infusion as usually done in Digital Subtraction Angiography (DSA). Nor is it necessary to acquire two different images with different X ray spectrum at two exposures as usually done in Dual Energy Subtraction (DES) techniques. The angiographic setting of the present invention comprises a pixelated area detector that detects the X rays. Any detector technology known in the art can be used in the apparatus of the present invention.

Each detector element is coupled to processing electronics, comprising amplification, shaping and comparing the photon signals to at least two thresholds. Signals below the lowest threshold are considered noise (or Compton scattered radiation) and are not counted. Signals above each threshold (and below the next threshold) are counted separately to form an image corresponding to energy bin. At least two images are taken of the patient lying in the angiographic setting of the present invention: for low energies and for high energies, in case two energy bins are selected.

The high energy image is then normalized, if necessary, and subtracted from the low energy image (or visa versa). In a fluoroscopy mode, the subtracted images are displayed to the operator at a small time lag from acquisition. The results as will be shown herein after in a simulation, are high contrast images of the arteries with surrounding tissues subtracted. The images are substantial motion artifacts free since the low energy and the high energy images are acquired simultaneously.

The method can be used in coronary angiography to eliminate heart motion artifacts and peripheral angiography to eliminate breathing or other motion artifacts. It can be used in non-cardiovascular applications too. For example: dynamic orthopedic imaging of bones or joint during motion, amplification of micro-calcifications in Mammography, etc.

Reference is now made to FIG. 1 illustrating a subject examined in an apparatus for improved imaging in accordance with a preferred embodiment of the present invention. The general layout of cardiac angiography system 100 may be similar to conventional angiographic systems known in the art. Patient 102 is lying on a support 104. X ray source 106 that comprises an X ray tube, collimators and filters as known in the art (the interior of the X ray source is not shown in the figure in details) is mounted on a mechanical gantry such as a C arm 108. However, other mechanical geometries are also possible. The X ray tube is energized by a generator (not shown in the Figure) to provide X ray beam, which is collimated to cover the heart of patient 102. Optionally, the X ray tube is provided with tungsten target, it is energized by voltage of 100 to 120 kV and the beam is filtered to remove photons below energy of 20 kV.

A sensor system 110 is disposed on C arm 108. Sensor system 110 receives X radiation attenuated by the body of patient 102. Sensor system 110 may be used with or without antiscatter grid positioned in front of it. Output data of sensor system 110 is transmitted to acquisition system and workstation 112, processed to yield images as will be described hereinafter, and optionally displayed in real time on an in-room monitor 114.

During operation, the coronary arteries of patient 102 may be infused with contrast agent such as Iodine so as to amplify the image of blood vessels. Various interventional devices such as catheters, angioplasty balloons and stents may be present in the imaging field and viewed as well. In a typical application, the X ray tube is energized only when the operator wishes to view projection images and the images are displayed at a rate of 30 images per second.

Figure 2:
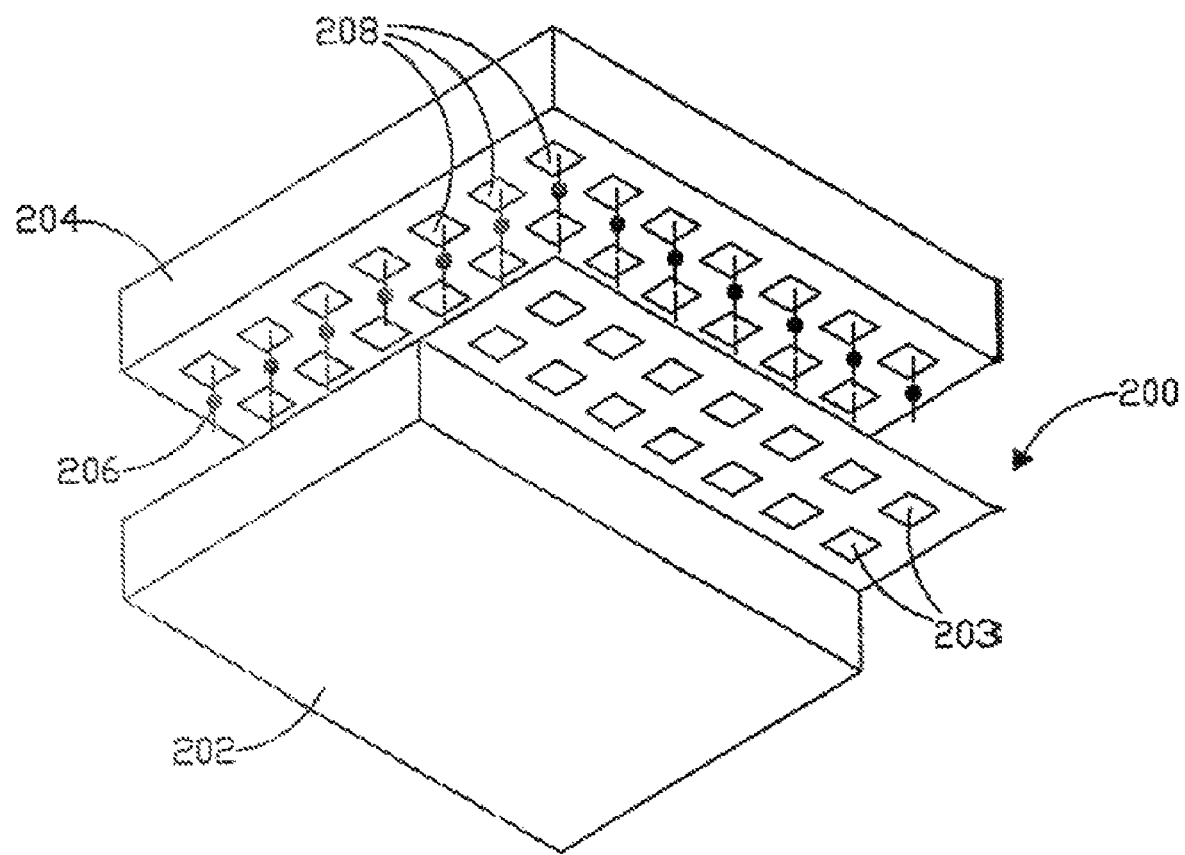
FIG. 2 illustrates a schematic layout of an X ray sensor incorporated in an apparatus for improved imaging in accordance with a preferred embodiment of the present invention.

Reference is now made to FIG. 2 illustrating a schematic layout of an X ray sensor useful in an apparatus for improved imaging in accordance with a preferred embodiment of the present invention. As shown in FIG. 1, sensor system 110 is positioned close to the patient's chest so as to receive the X ray radiation attenuated by the body of patient 102. The sensor system can be one of several sensors. FIG. 2 teaches a sensor 200 that is built of several layers. Detector chip 202 is used to stop X radiation and converts the X ray photon energy to change. Preferably, detector chip 202 is pixilated, namely divided to area elemnts 203. In a preferred embodiment, the over-all detector area is 200 mm×200 mm, and there are 1000×1000 detector elements so each element is 200 μm×200 μm in size. Optionally, detector chip 202 is composed of multiple modules, each of smaller dimensions. For example, if modules of 50 mm×50 mm are used, each having 250×250 area elements, the entire detector chip will have 16 modules. The operation of detector chip 202 and other optional embodiments are described herein after.

Several alternatives are known in the art for the construction of detector chip 202. According to one alternative, the detector chip is made of a semiconductor material such as Cadmium Zinc Telluride (CZT) as described e.g. in the following publications: "CZT pixel-detectors equipped with effective Ohmic contacts their spectroscopic performance and the engima of why they thus behave"; U. El Hanany, A. Shahar and A. Tsigelman. (Keynote Address) Hard X-Ray, Gamma-Ray, and Neutron Physics. Proceedings of SPIE, Denver, Colo., 19-23 Jul. 1999; "CZT pixel detector modules for medical imaging and nuclear spectrometry"; U. El Hanany, A. Shahar and A. Tsigelman. Presented at the 11th International Workshop on Room Temprature Semiconductor X-and Gamma Detectors; Vienna Oct. 11-15 1999; "Development of IMARAD CZT Detectors with PIN Contacts"; Narita, T., Bloser, P., Grindlay, J., Jenkins, J., and Yao, H. 1999, Proc SPIE 3768; "design and Preliminary Tests of a Prototype CZT Imaging Array"; T. Narita, J. E, Grindlay, J. A. Jenkins, M. Perrin, D. Marrone, R. Murray and B. Connell 2002, Proc SPIE, 4497, 79, brought herein as references.

The CZT detector to be used in the embodiment of the present invention is pixilated to elements of typically 200 μm×200 μm as discussed earlier. The division of the CZT wafer to pixels is accomplished by deposition of pixilated metallic electrodes on one face whereas there is a common metallic electrode covering the opposite face. Readout chips are electronic devices used to receive the charges from the multiple detector elements and convert them into digital data. Readout chip 204 is divided into channels 208, each processing the signals from one detector element 203. Readout chip 204 may include the same number of channels as the elements in one detector module so one detector chip 202 interconnects to one element of readout chip 204, or optionally other configurations may apply like several readout chips for one detector module.

Optionally, readout chip 204 is divided to channels with the same geometrical layout as detector chip 202 and the two chips are interconnected directly as shown in FIG. 2. The interconnection 206 of detector chip 202 to readout chip 204 is done by techniques known in the art as flip chip bonding or bump bonding.

According to another alternative (not shown in FIG. 2), one or more readout chips can mounted on an intermediate substrate made to interconnect to the detector chip. The substrate may be a multiplayer printed circuit board.

Figure 5:
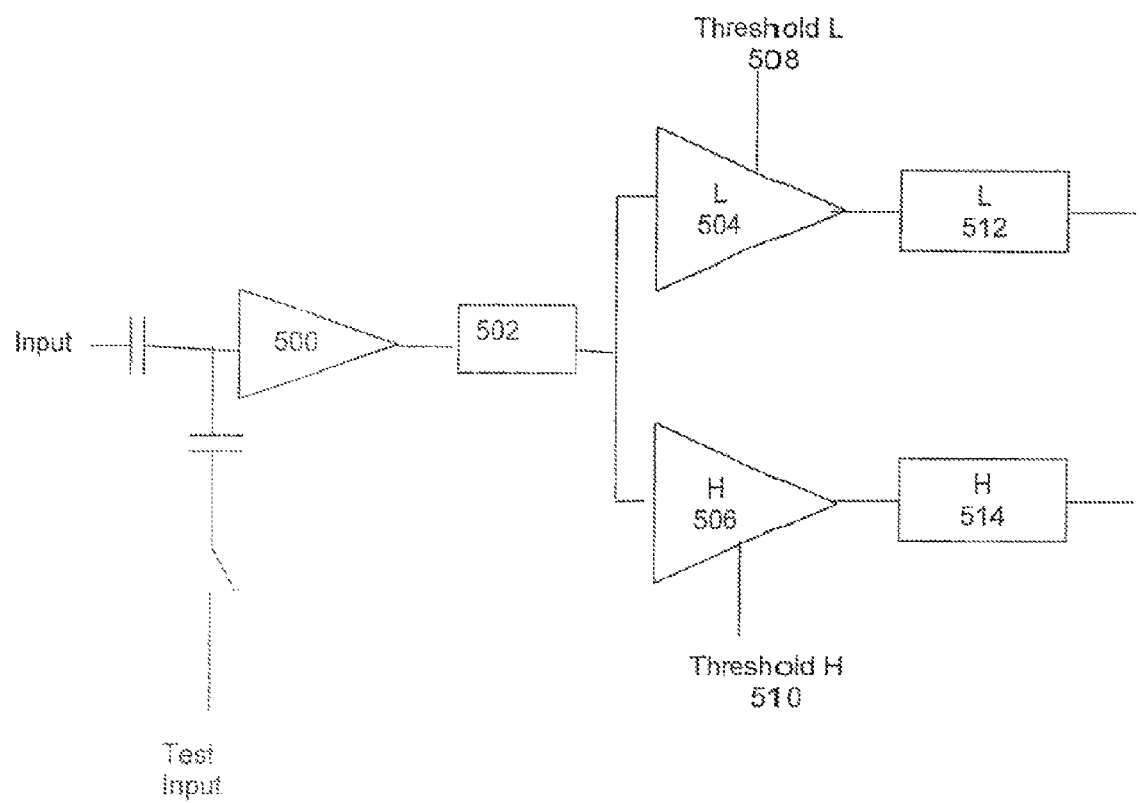
FIG. 5 illustrates a diagrammatic layout of a single channel in a readout chip in according with a preferred embodiment of the present invention.

Reference is also made to FIG. 5, illustrating a diagrammatic layout of a single channel in readout chip 204 in accordance with a preferred embodiment of the present invention. Charge generated in detector chip 202 due to the absorption of X ray photon is amplified by preamplifier 500 and shaped by pulse shaper circuit 502. The resulting shaped pulse, whose height is proportional to the energy of the absorbed photon, is fed into pulse height discriminators L 504 and discriminator H 506. Each of the discriminators 504 and 506 is loaded with a pre-set threshold level 508 and 510, respectively, such that the discriminator outputs a pulse if the input pulse level is above the discriminator level. Counters 512 and 514 count the number of events detected in discriminators 504 and 506, respectively. In a typical application, the threshold to discriminator L 504 may be set at a level corresponding to 30 keV photon energy and the threshold to discriminator H 506 may be set at a level corresponding to 60 keV photon energy. Therefore counter 512 measures the number of photons detected by the corresponding detector element with energy above 30 keV and counter 514 measures the number of photons detected by the corresponding detector element with energy above 60 keV. Digital count numbers of counters 512 and 514 are read periodically by external circuit (not shown in the Figures) and reset to zero, so as to start a new accumulation. In a typical applications, the counters are read and reset 30 times a second.

Optionally, a circuit (now shown) is provided to subtract the digital output of counter 514 from the output counter 512, so as to yield the number of counts in the energy bin between the low threshold level and the high threshold level. The combined outputs of all elements in the array yield two digital images of the radiation intensity levels within the low energy bin and the high energy bin.

It is noted that more than two discriminators and counters may be used to yield more than two energy bins data and different energy ranges than described herein above may apply. Any number of energy bins produced by a corresponding amount of discriminators and counters are covered in the scope of the present invention. In particular, in certain clinical settings, lower energy X rays may be used and the energy bins may be set below and above the K edge energy of Iodine or other element of interest.

Returning to FIG. 2, readout chip 204 is similar in design and construction to a number of devices developed and published in recent years for medical imaging and astrophysics applications. The following examples are provided herein as references: Medipix2, a 64 k pixel readout chip with 55 μm square elements working in single photon counting mode, X. Llopart, M. Campbell, R. Dinapoll, D. SanSegundo, E. Pernigotti, Proc. of the IEEE Nuclear Science Symposium and Medical Imaging Conference, San Diego, Calif., Nov. 4-10, 201, M7-4, accepted for publication in IEEE Trans. Nucl. Sci. This article describes an electronic chip called Medipix 2 that includes 64 k processing channels. Each channel receives charge input from one detector element. The input is amplified, shaped and fed to two programmable threshold discriminators. Using logic circuits and shift registers, the device counts the number of X ray photons hitting the detector elements in a given time frame at two energy windows. Namely, the output of each channel is the numbers of photons with energy between a low threshold and a high threshold and the number of photons with energy above the high threshold.

The readout electronics in the sensor 200 may resemble Medipix 2 chip, however, there are some modifications so as to allow sensor 200 to be incorporated in the apparatus for improved angiographic imaging of the present invention. The number of channels 208 per single chip 204 is preferably optimized to match the number of channels in detector chip 202 (or integer fraction thereof). The number of discriminators can be larger than 2, yielding output data for more than 2 energy bins. Moreover, readout chip 204 has geometrical dimensions that facilitate its interconnection to detector chip 202 or to an intermediate substrate that is placed between the chips.

Preferably, control and readout connections are provided at the back face of readout chip 204 (where the input contacts are disposed on the front face) so as to facilitate tilling of many chips side by side.

It should be noted that other readout chip designs can be employed in the apparatus for improved angiographic and other readout chips are covered by the scope of the present invention as long as they provide the desired functionality.

Figure 3A:
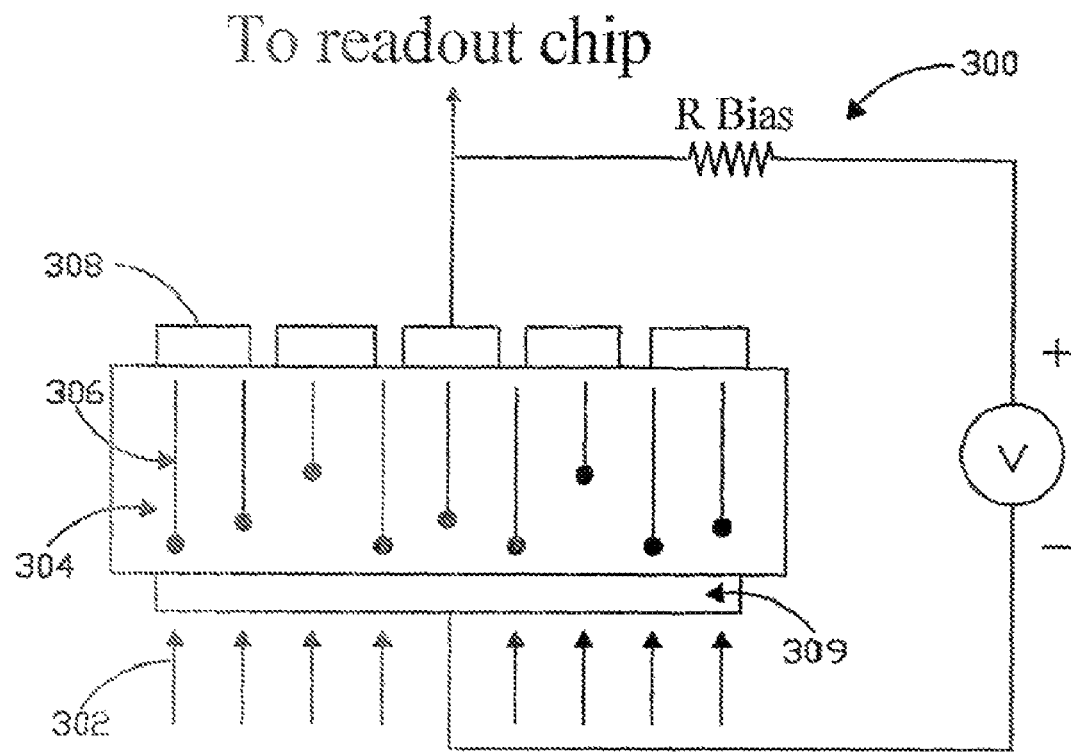
FIG. 3a illustrates a schematic description of the operation of a detector to be used in the apparatus shown in FIG. 1 in accordance with a preferred embodiment of the present invention.

Reference is now made to FIG. 3a illustrating a schematic description of the operation of a detector to be used in the apparatus shown in FIG. 1 in accordance with a preferred embodiment of the present invention. X rays 302 that are transmitted through the patient and impinge on detector chip 300 are stopped in semiconductor material (such as CZT) 304 and are converted to charge 306, which migrates under external bias to electrodes 308. Electrode 309 is a common electrode for the whole array. The changes are injected to readout electronics (not shown in FIG. 3a). For simplicity, only one electrode 308 is shown connected to readout electronics although all electrodes are connected, each of separate readout electronics channel. For the present application, where detection of X rays up to energy of 120 KeV is desired, CZT thickness of typically 5 mm is needed although a thicker or thinner CZT wafer can be used and external bias of typically 600V is applied.

Figure 3B:
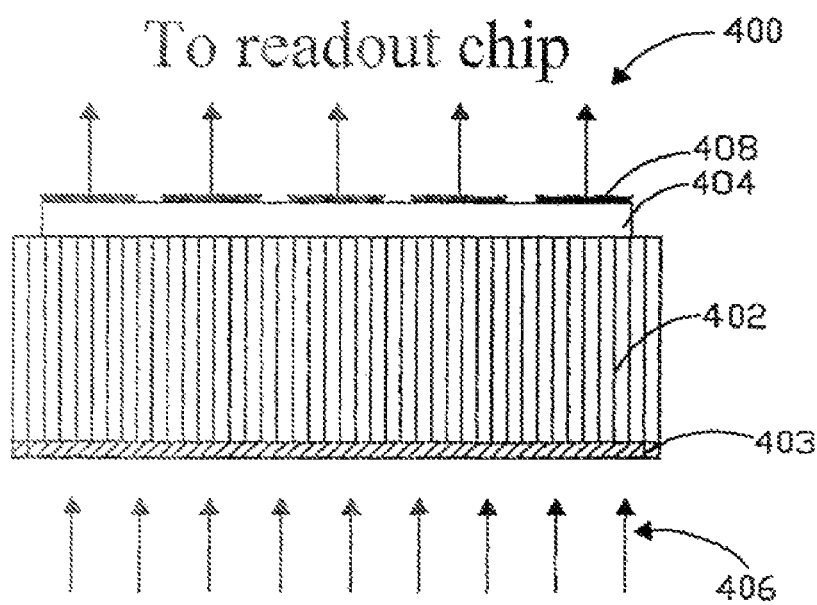
FIG. 3b illustrates a schematic description of the operation of another detector to be used in the apparatus shown in FIG. 1 in accordance with another preferred embodiment of the present invention.

Reference is now made to FIG. 3b illustrating a schematic description of the operation of another detector to be used in the apparatus shown in FIG. 1 in accordance with another preferred embodiment of the present invention. According to the alternative detector chip shown in FIG. 3b, detector chip 400 comprises a plate of scintillator material 402 such as 0.5 mm to 1 mm thick layer of CsI, coated with light reflecting material 403 and optically interfaced to a pixilated array of silicon photodiodes 404. X rays 406 are stopped in scintillator material 402 and are being converted into light. If CsI is used as scintillator material, it is preferably grown in column structure so as to direct the light in a direction perpendicular to the plate. The light is converted to charge by the array of photodiodes 404. Photodiodes 404 may be operated with or without bias, depending on the design of the photodiode, as known in the art. The charges are then injected to readout electronics through electrodes 408. It shown be noted that photodiode 404 can be any photodiode known in the art such as back-illuminated photodiode.

Figure 4:
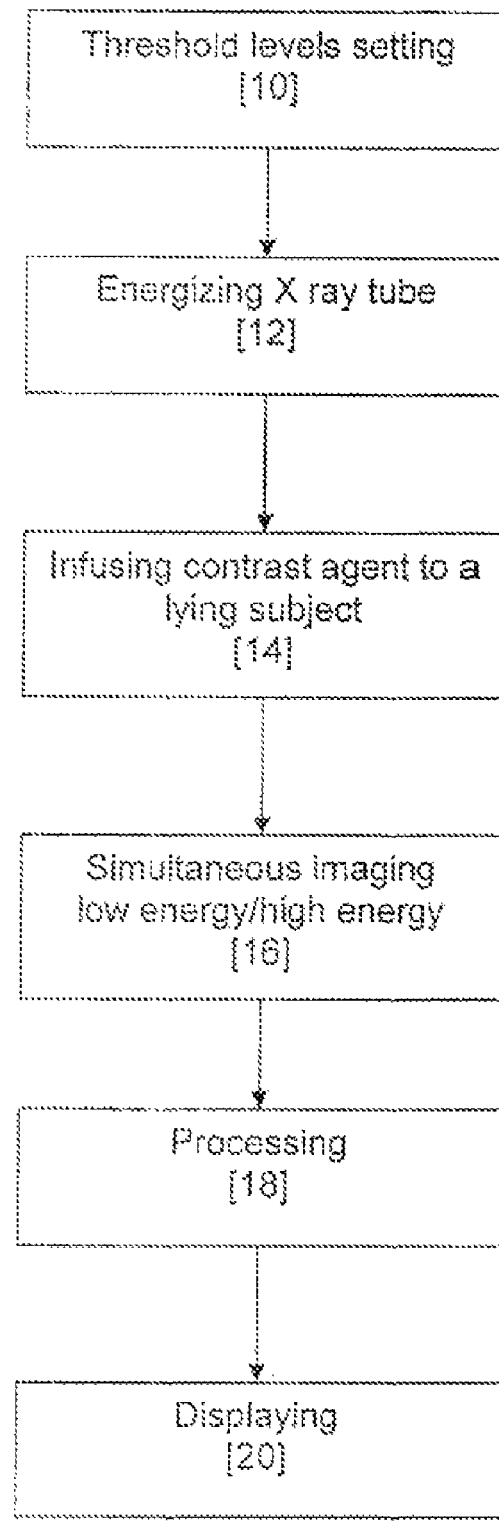
FIG. 4 illustrates the method of improved angiographic X ray imaging in accordance with a preferred embodiment of the present invention.

Reference is now made to FIG. 4 illustrating the method of improved angiographic X ray imaging in accordance with a preferred embodiment of the present invention. According to the method of improved angiographic imaging of the present invention, before imaging a patient, the threshold levels for the discriminators for each channel in the sensor have to be set [10]. This can be done using radioactive sources. Assuming for example that two discriminators are provided and it is desired to set them at energy levels of 30 keV and 60 keV. The following procedure is then taken (this procedure is exemplary and is provided solely for illustrational purposes):

First, the detector chip is irradiated with a $^{137}$Cs radioactive source. The source emits, among other radiation, X ray photons at energy of 32 keV. The threshold level of the low level discriminator is gradually increased for each readout channel while the output counting rate is monitored. As the discriminator level increases over 32 keV, the count rate drops. The 30 keV threshold is set at a level slightly below the drop level. Different readout channels may have different absolute threshold setting because of different amplifier offset and gain.

Secondly and similarly, the detector is irradiated by a $^{241}$Am radioactive source, which emits gamma rays of 59.5 keV. The threshold level for the high level discriminator is set at the level at which the radiation counts rate drops.

Other radioactive sources may be used if more discriminator levels or different levels are desired. Alternatively, the gain and offset for each channel are determined once using two energy levels and other discriminator levels are determined by interpolation or extrapolation.

In a typical application of the apparatus of the present invention, for imaging the coronary arteries of a subject, the subject is lying in the angiographic setting as shown in FIG. 1. The X ray tube is energized [12] by 120 kV and the myocardium is imaged [16] while contrast agent is infused to the coronary arteries of the subject [14]. Single photon counting data is acquired with the detector while two thresholds are set to form images for photons in the energy windows from 30 keV to 60 keV (low energy image) and 60 kev to 120 keV (high energy image). Optionally, the readout electronics is read every 33 msec, providing 30 images a second. The images can be processed [18] and displayed [20] in any of the following ways but not limited thereof.

1. The low energy and high energy images summed. Effectively, all photons above the lower threshold are counted. The images have an advantage over prior art of higher contrast and lower noise.
2. The data is binned to form low energy image and high energy image. Both images may be displayed. However, the low energy image has a higher contrast so it is more useful for visualizing the coronary arteries.
3. The high energy image is normalized to the low energy image and subtracted from it (optionally the normalization is done on image areas without arteries). The result is an image without the surrounding tissues. Only the coronary arteries filled with contrast agent and foreign objects (such as catheters, stents, angiography balloons marked with X ray opaque materials) are observed.
4. Only a pre-set fraction of the high energy image is subtracted from the low energy image in order to keep some surrounding tissue shadow in the background of the image for land marking.

It should be recognized that more energy windows can be used with various binning schemes and various subtraction schemes can be used to optimize the contrast versus noise. Other schemes are covered by the scope of the present invention.

The following table provides the results of a Monte Carlo calculation of the images obtained for a 2 mm diameter artery filled with iodine contrast agent at iodine concentration of 100 mg/ml surrounded by chest and myocardium tissues. The surrounding tissues are simulated by a mathematical chest phantom consisting of layers of aluminum, acrylic and air simulating typical X ray absorption in the chest. The X ray tube is assumed to have tungsten target, operation voltage of 120 kV and filtering equivalent to 2.5 mm aluminum. The Monte Carlo simulation includes the effects of primary scattering without scatter grid in front of the detector.

The contrast is defined as the number of detected X ray photons per unit area near the artery minus the number of photons per unit area in the artery, all normalized to the average number of photons.

| Detection mode | Contrast % |
| --- | --- |
| Prior art - integrating all charges | 11.7 |
| Photon counting w/o energy discrimination | 14.7 |
| Photon counting: 10-60 keV | 23 |
| Photon counting: 60-120 keV | 5.8 |
| Photon counting: 10-30 keV | 17.4 |
| Photon counting: 30-50 keV | 30 |
| Photon counting: 50-70 keV | 12.5 |
| Photon counting: 70-90 keV | 5 |
| Photon counting: 90-120 keV | 1.5 |

The simulation demonstrates that the contrast for photon counting imaging is better than for charge integration even without energy binning. When dividing the data to two energy bins, which have similar total number of photons and image noise, the low energy image has about twice the contrast of prior art image whereas the high energy image displays much lower contrast. Binning the data to several narrower energy windows shows that the best contrast is observed at the energy range above the iodine K edge.

According to the simulation, the statistical image noise in the photon counting case is somewhat lower than the noise in prior art imaging. In addition, the photon counting system does not suffer from electronic noise which is present in prior art images.

The advantages of the apparatus for improved angiographic imaging of the present invention over prior art are:

1. The dual energy subtracted images amplify the visualization of coronary arteries without having motion artifacts since the low and high energy images are acquired simultaneously.
2. Since the image contrast is higher, it is possible to apply substantially less radiation dose and still have good visualization that can be accurately interpreted.
3. Since the image contrast is higher, it is possible to apply less contrast agent.

The invention is described herein in the context of coronary angiography; however, it is useful also in the context of general angiography in other parts of the vascular systems.

It should be clear that the description of the embodiments and attached Figures set forth in this specification serves only for a better understanding of the invention, without limiting its scope as covered by the following Claims.

It should also be clear that a person skilled in the art, after reading the present specification can make adjustments or amendments to the attached Figures and above described embodiments that would still be covered by the following Claims.

The invention claimed is:

1. An apparatus for improved dynamic angiographic X ray imaging of a subject's body infused with contrast agent, said apparatus comprising:

an x ray source capable of emitting an X ray beam directed to pass through the subject's body wherein said X ray beam is polychromatic;

a sensor system capable of receiving an attenuated X ray beam that passed through the subject's body, wherein said sensor comprises:

a detector divided into a plurality of detection elements, wherein each one of said plurality of detection elements is capable of converting photon energy of a portion of said attenuated X ray beam into electric charges; and at least one readout chip divided into a plurality of channels wherein each one of said plurality of channels is electronically connected to one of said plurality of detection elements and wherein each one of said plurality of channels is capable of converting said electric charges into digital data and wherein said at least one readout chip is provided with at least two programmable threshold discriminators;

an acquisition system capable of receiving said digital data from said sensor and generate at least two electronic representations wherein one of said at least two electronic representations is attained from low energy photons and another of said at least two electronic representations is attained from high energy photons wherein said at least two electronic representations are measured simultaneously at the subject and at a certain position of said X ray beam source;

a processor capable of manipulating said at least two electronic representations into at least one image; and a display capable of displaying said at least one image, whereby said at least one image attained from at least two energy bins amplify the appearance of the contrast agent in blood vessels in respect with surrounding tissues of the subject's body.

2. The apparatus as claimed in claim 1, wherein said detector is a pixel detector chip made of a semiconductor material.

3. The apparatus as claimed in claim 1, wherein said detector is a detector chip made of a scintillator material coupled to light to charge conversion elements.

4. The apparatus as claimed in claim 3, wherein said scintillator material is CsI(Na) or CsI(Tl).

5. The apparatus as claimed in claim 3, wherein said light to charge conversion elements comprise an array of Si photodiodes.

6. The apparatus as claimed in claim 1, wherein said at least one readout chip is provided with the at least two programmable threshold discriminators so as to allow each one of said plurality of channels to output a representation of a number of photons carrying energy below a predetermined threshold, between said predetermined threshold and a higher predetermined threshold, and above said higher predetermined threshold.

7. The apparatus as claimed in claim 6, wherein said at least one readout chip is provided with a preamplifier and a pulse shaper.

8. The apparatus as claimed in claim 6, further comprising at least two counters adapted to count events detected in the at least two programmable threshold discriminators.

9. The apparatus as claimed in claim 1, wherein the infused contrast agent is Iodine solution.

10. The apparatus as claimed in claim 1, wherein said low energy photons are set below the K edge of the contrast agent and said high energy photons are set above the K edge of the contrast agent.

11. The apparatus as claimed in claim 1, wherein said low energy photons are set just above the K edge of the contrast agent and said high energy photons are set further above the K edge of the contrast agent.

12. The apparatus as claimed in claim 1, wherein a portion of the subject's body is the chest and wherein coronary blood vessels are imaged.

13. The apparatus as claimed in claim 12, wherein a difference image of said low energy photons and said high energy photons presentations are generated and displayed so as to amplify the appearance of the contrast agent, wherein said difference image is motion artifacts prone.

14. The apparatus as claimed in claim 1, wherein a portion of the subject's body is the head and neck and wherein cranial or cranial supply blood vessels are imaged.

15. The apparatus as claimed in claim 1, wherein peripheral blood vessels are imaged.

16. The apparatus as claimed in claim 1, wherein images are acquired, processed and displayed multiple times every second at a short time lag from acquisition so as to generate real time imaging of the subject's body.

17. The apparatus as claimed in claim 1, wherein said processor is capable of processing said at least two electronic representations by producing a normalized high energy image of one of the electronic representations attained from high energy photons to a different electronic representation attained from low energy photons and subtraction of said normalized high energy representation from said different electronic representation.

18. The apparatus as claimed in claim 1, wherein said processor is adapted to process said at least two electronic representations by producing a normalized high energy image of one of the electronic representation attained from high energy photons to a different electronic representation attained from low energy photons and subtraction of a predetermined fraction of the normalized high energy image from said different electronic representation.

19. A dynamic method for producing images of improved X ray angiography of a subject's body, said method comprising:
    directing polychromatic X ray beam to pass through the subject's body;
    positioning a sensor system adapted to receive attenuated X rays that passed through said subject's body, said sensor system comprising a detector divided into a plurality of detection elements, wherein each one of said plurality of detection elements is adapted to convert photon energy of a portion of said attenuated X rays into electric charges, and at least one readout chip provided with at least two discriminators, said at least one readout chip divided into a plurality of channels wherein each one of said plurality of channels is electronically connected to one of said plurality of detection elements and wherein each one of said plurality of channels is capable of converting said electric charges into digital data;
    setting threshold levels for said at least two discriminators for each one of said plurality of channels at least once;
    injecting a contrast agent into blood vessels of the subject's body;
    positioning said subject so that X ray beam passes through the body of the subject and attenuated X rays that passed through the subject's body are received by said sensor system;
    acquiring single photon counting data from a single X-ray pulse so as to simultaneously establish at least two images from at least one of low photon energy window and at least one of high energy window; and
    processing said at least two images so as to provide high contrast and motion artifact free image of the subject's blood vessels.

20. The method as claimed in claim 19, wherein said low energy window is set below the K edge of said contrast agent and said high energy window is set above the K edge of said contrast agent.

21. The method as claimed in claim 19, wherein said low energy window is set just above the K edge of said contrast agent and said high energy window is set further above the K edge of said contrast agent.

22. The method as claimed in claim 19, wherein setting threshold levels comprises irradiating said detection elements with radiation of at least two predetermined energy levels while monitoring output counting rate so as to set the threshold level slightly below the level in which the count rate drops.

23. The method as claimed in claim 22, wherein said detection elements are irradiated with X ray photons at 32 keV for setting one threshold level and with gamma rays of 59.5 keV for setting a second threshold level.

24. The method as claimed in claim 19, wherein said processing said at least two images comprises
    normalizing one of said at least two images attained from said high energy window to a different image attained from said low energy window so as to acquire normalized high energy image;
    subtracting said normalized high energy image from said different image attained from said low energy window.

25. The method as claimed in claim 19, wherein said processing said at least two images comprises normalizing one of said at least two images attained from said high energy window to a different image attained from said low energy window so as to acquire normalized high energy image;

subtracting a pre-determined fraction of the normalized high energy image from said different image.

26. The method as claimed in claim 19, wherein the method is used to image the subject's coronary blood vessels.

27. The method as claimed in claim 19, wherein the subject's body is the head and neck and wherein cranial or cranial supply blood vessels are imaged.

28. The method as claimed in claim 19, wherein peripheral blood vessels are imaged.

* * * * *